United States Patent
Marshall et al.

(10) Patent No.: US 6,580,020 B1
(45) Date of Patent: Jun. 17, 2003

(54) CORN HYBRID P741

(75) Inventors: Lorelei C. Marshall, Iowa City, IA (US); Terry J. Foley, Williamsburg, IA (US)

(73) Assignee: Optimum Quality Grains, L.L.C., Johnston, IA (US)

( * ) Notice: Subject to any disclaimer, the term of this patent is extended or adjusted under 35 U.S.C. 154(b) by 93 days.

(21) Appl. No.: 09/705,521

(22) Filed: Nov. 2, 2000

(51) Int. Cl.[7] .............. A01H 1/00; A01H 5/00; A01H 5/10; A01H 1/02; C12N 5/04
(52) U.S. Cl. ............... 800/320.1; 435/412; 800/271; 800/275; 800/260; 800/298
(58) Field of Search ............ 800/275, 320.1, 800/298, 271, 260, 274, 264; 435/412, 430, 424

(56) References Cited

U.S. PATENT DOCUMENTS 5,824,854 A * 10/1998 Bergquist .................. 800/271
6,284,954 B1 * 9/2001 Marshall et al. ......... 800/320.1
6,288,311 B1 * 9/2001 Marshall et al. ......... 800/320.1

OTHER PUBLICATIONS

Rashid et al 1992, J. Heredity 83:130–134.*
Kraft et al 2000, Theor. Appl. Genet. 101:323–326.*
Eshed et al 1996, Genetics 143:1807–1817.*
Fehr et al 1987, pp 417–427, In: Principles of Cultivar Development, vol. 1. Theory and Technique. MacMillan Publishing Co., New York.*

El–Habitab et al 1985, A. Acker–Planzenb. 154(4):267–275.*

Kinman et al 1945, J. Amer. Soc. Agronomy 37(5):341–351.*

* cited by examiner

Primary Examiner—David T. Fox
Assistant Examiner—David H. Kruse
(74) Attorney, Agent, or Firm—Bullwinkel Partners, Ltd.

(57) ABSTRACT

A synthetic hybrid corn line having the designation P741, produced by crossing the inbred Qx47 and the synthetic P732. P741 imparts a high oil level in the grain of certain male sterile hybrids when used as a pollinator. P741 is also gives higher test weight in grain than other pollinators of similar oil levels when used in the TOPCROSS® grain production system. P741 has shown excellent productivity in TC BLEND® seed blends of medium to late season adaptability. This invention thus relates to the seeds, plants and plant parts of P741 and its components, to plants regenerated from tissue culture of the plants of P741, to a method of producing P741, and to a method for producing high oil grain using P741 as a pollinator.

9 Claims, No Drawings

CORN HYBRID P741

FIELD OF THE INVENTION

This invention is in the field of maize breeding. Specifically, this invention relates to a novel corn hybrid having the designation P741.

BACKGROUND OF THE INVENTION

Principles of conventional plant breeding Most of the commercial corn produced in the United States is produced from hybrid seed. The production of hybrid seed first requires the development of elite corn inbred lines that possess good combining ability to produce agronomically superior hybrids. The majority of hybrid seed produced in the United States is of the single cross type, wherein two inbred lines are intermated, or crossed, to produce what is termed seed of an $F_1$ single cross hybrid. This seed is then sold to commercial grain growers who plant the seed and harvest the second generation, or $F_2$ grain, for use on farm or for commercial sale.

The production of conventional single cross hybrid seed involves controlling the direction of pollination from one inbred to the other to assure the production of predominantly hybrid (cross pollinated) seed. Typically, directed pollination is accomplished by interplanting separate rows of female corn plants with male corn plants. The female corn plants that are male sterile may be produced by genetic mechanisms which render the corn tassel or pollen nonfunctional or by detasseling the plants in the field.

The development of corn hybrids requires the development of homozygous inbred lines, the crossing of these lines, and the evaluation of the crosses. Pedigree breeding, backcross conversion and recurrent selection breeding methods are used to develop the inbred lines from breeding populations. These breeding methods combine desirable traits from two or more inbred lines or various broad-based populations into breeding pools from which new inbred lines are developed by inbreeding or random mating and selection of desired phenotypes. The new inbreds are crossed with other inbreds and the resulting hybrids are evaluated to determine which have commercial value and agronomic usefulness.

The objective of typical plant breeding is to develop a hybrid with desirable traits such as resistance to diseases and insects, herbicide tolerance, tolerance to heat and drought, reduction of time to crop maturity, and improved agronomic quality. Because many crops are harvested mechanically, uniformity of plant characteristics such as germination time, stand establishment, growth rate, and fruit/seed size are also desirable.

The problem with conventional breeding techniques is that there are several grain quality traits, such as high oil content, that cannot readily be obtained in a high-yielding single cross hybrid. One solution to this problem has been proposed by Bergquist et al. in U.S. Pat. Nos. 5,704,160 and 5,706,603, incorporated herein by reference. A primary aspect of this method, known as the TOPCROSS® grain production system, is the interplanting of a pollinator corn plant possessing the characteristics for significantly increasing oil level in the resulting grain, with a male sterile hybrid corn plant. The resulting grain possesses an oil content much higher than would be expected for self- or cross-pollination of the fertile version of the hybrid corn plant.

In practice, the seed of the pollinator with improved grain quality traits is blended in small amounts with seed of an elite male sterile grain parent hybrid, but with sufficient pollinator seed to permit abundant pollen production for fertilization of the male sterile grain parent hybrid. The relatively low ratio of pollinator seed to male sterile grain parent seed (typically less than one pollinator plant to every three grain parent plants) takes advantage of the higher grain yield potential of the elite grain parent hybrid while assuring a sufficient population of pollinator plants to pollinate the male sterile grain parent plants.

Critical to the success of the TOPCROSS® grain production system is the use of a pollinator capable of enhancing the grain quality traits of the $F_1$ grain. P741 was developed for this purpose. The present invention, when used as a pollinator, imparts high oil content accompanied by high test weight to the resulting $F_1$ grain without significant loss of yield.

SUMMARY

According to the invention, there is provided a novel corn hybrid, designated P741, that when used to pollinate an elite male sterile hybrid grain parent, produces commercial grain exhibiting improved quality grain traits, including high oil along with good test weight.

P741 is a medium-late flowering synthetic hybrid, broadly adapted to the corn growing areas of the Central United States. Grain from P741 has expressed high oil and excellent test weight.

The invention thus relates to the seeds, plants and plant parts of P741; to tissue culture comprising regenerable cells of a plant part of P741; to plants regenerated from regenerable cells of the tissue culture of P741; to corn plants having substantially all the phenotypic, genotypic and/or physiological characteristics of P741; to the method of producing P741; to grain or seed produced by crossing P741 with a different corn plant wherein the resulting progeny have one-half the nuclear genotype of P741; to seed blends of P741 and male sterile corn hybrids; to a method of producing high oil grain using P741 as a pollinator in a TC BLEND® seed mixture; and to corn plants produced or derived from P741 seed wherein the corn plants have the ability to impart high oil or other grain quality traits to the $F_1$ grain when these P741-derivatives are used in the TOPCROSS® grain production system.

DEFINITIONS

In the description that follows, a number of terms are used. In order to provide a clear and consistent understanding of the specification and claims, including the scope to be given such terms, the following definitions are provided:

Combining Ability. The ability of a genetic strain, when crossed with another strain, to produce a high proportion of desirable individuals.

Endosperm. The nutritive tissue formed within the embryo sac in seed plants. It commonly arises following the fertilization of the diploid polar nucleus by one male sperm.

Express. To manifest a genetic character trait.

$F_1$. The first generation of a cross.

$F_2$. The second filial generation obtained by self-fertilization or crossing inter se of $F_1$ individuals. Subsequent generations are $F_3$, $F_4$, $F_5$, etc.

Genotype. The fundamental genetic constitution of an organism.

Grain. Mature corn kernels produced by commercial growers for purposes other than growing or reproducing the species.

Grain Parent. Male sterile, elite hybrid that comprises a large majority of the plants in a grain production field.

Grain Quality Trait. Any attribute of grain that is of commercial value. Such traits relate to the intermediate or final use of grain and include but are limited to the quantity or quality of oil, protein, starch, pigmentation, and fiber found in corn grain. Such traits also encompass physical attributes of the grain itself, such as grain texture, size, or hardness, among others. Certain of these compositional or physical attributes of grain correlate with functional attributes as well which are of commercial importance, such as susceptibility to breakage and spoilage, among others.

Homozygous. A genetic condition existing when identical alleles reside at corresponding loci on homologous chromosomes.

Hybrid. (1) The progeny of a cross fertilization between parents belonging to different genotypes. (2) The first generation offspring of a cross between two individuals differing in one or more genes. (3) A hybrid is the result of a cross between two or more components.

Inbred or Inbred Line. A substantially homozygous individual, variety or line produced by continued inbreeding. In plant breeding a nearly homozygous line usually originates by continued self-fertilization, accompanied by selection.

Kernel. The corn caryopsis comprising a mature embryo and endosperm which are products of double fertilization.

Line. (1) A group of individuals from a common ancestry. (2) A narrowly defined group that is a variety.

Male Sterile. A condition in which pollen is absent or non-functional in flowering plants.

Percent Oil. The oil concentration of a corn kernel, typically determined at 0% moisture.

Phenotype. (1) Physical or external appearance of an organism as contrasted with its genetic constitution (=genotype); (2) a group of organisms with similar physical or external makeup; (3) the observed character of an individual without reference to its genetic nature.

Pollen. A structure which gives rise to two haploid sperm nuclei which fuse with the egg nucleus and polar nuclei found in the ovule to give rise to the embryo and endosperm of the mature corn kernel.

Pollinators. Male fertile corn plants used to pollinate male sterile hybrid corn plants in order to produce a Grain Quality Trait in the resulting F1 grain.

Population. In genetics, a community of individuals which share a common gene pool.

Seed. Mature corn kernels produced for the purpose of propagating the species.

Single Cross. A cross between two different genotypes, each of which may be an inbred or synthetic.

Synthetic (Population). A genetically heterogeneous collection of plants of known ancestry created by the intermating of any combination of inbreds, hybrids, varieties, populations, races or other synthetics.

Synthetic Hybrid. A hybrid in which one or more genotypes used to make the hybrid is a synthetic.

TC BLEND®. A registered trademark of E.I. duPont de Nemours and Company for a physical mixture of two or more types of seed utilized in the TOPCROSS® grain production system.

Test Weight. The measure of the weight of the grain in pounds for a given volume (bushel) adjusted for percent moisture at harvest.

TOPCROSS®. A registered trademark of E.I. duPont de Nemours and Company for a grain production system and the high oil corn seed used therein.

Yield (Bushels/Acre). The yield in bushels/acre is the actual yield of the grain at harvest adjusted to 15.5% moisture. One bushel is equal to 56 pounds.

DETAILED DESCRIPTION OF THE INVENTION

P741 is a high oil synthetic hybrid having superior agronomic characteristics and the ability to impart desirable grain quality traits to a first generation grain when used as a pollinator in the TOPCROSS® grain production system. P741 is adapted over a wide area of the Central region of the U.S. corn belt. P741 can be used advantageously in TC BLEND® seed blends with grain parents from approximately 112–118 relative maturity.

P741 is produced by crossing proprietary corn inbred line Qx47 with the proprietary corn synthetic P732. Either parent may be used as the female parent or the male parent. P741's parents have large, highly branched tassels.

Although P741's primary use would be as a pollinator in the TOPCROSS® grain production system with blends of medium to late maturing corn hybrid male sterile grain parents, it may also be crossed with other high oil pollinators to develop derived pollinators, for example by crossing to earlier or later pollinators for expanding the use of its genetics to wider maturity grain parents.

Comparison of P741 to Synthetic Hybrid LP57.1

LP57.1 is a synthetic hybrid described in Bergquist U.S. Pat. No. 5,824,854. The timing and duration of P741 flowering is very similar to LP57.1. The data in Table 1 indicate that P741 has pollen shedding dates similar to LP57.1, and thus can be used advantageously in TC BLEND® seed blends of medium to late maturity. Table 2 shows that the flowering of P741 matches well with the flowering of a variety of male sterile grain parents.

TABLE 1

Comparison of Pollen shedding for P741 and LP57.1
(Average of 1999–2000 Flowering observations on
the number of days from planting to 10%, 50% and 90% plants
shedding pollen)
(1999: 22 locations; 2000: 10 locations, 2 reps/loc)

| Pollinator | No. of days until 10% shedding | No. of days until 50% shedding | No. of days until 90% shedding |
|---|---|---|---|
| P741 | 65.9 | 68.1 | 69.8 |
| LP57.1 | 66.1 | 68.2 | 70.0 |

TABLE 2

Comparison of Flowering Observations for P741 and
Selected Grain Parent Silking Observations
(Note: flowering = pollen shed for P741 and
silking for the male-sterile hybrid grain parents)
(1999 date, 14 locations, 2 reps/location)

| | Days to flowering | | | Relative maturity for self-pollinated hybrid (days) |
|---|---|---|---|---|
| | 10% | 50% | 90% | |
| P741 | 63.9 | 66.1 | 67.9 | |
| HC33SDms × LH283 | 64.1 | 65.8 | 67.1 | 114 |
| LH200SDms × LH185 | 64.1 | 65.6 | 67.1 | 114 |
| LH198SDms × QH102 | 63.8 | 65.4 | 66.6 | 115 |

TABLE 2-continued

Comparison of Flowering Observations for P741 and
Selected Grain Parent Silking Observations
(Note: flowering = pollen shed for P741 and
silking for the male-sterile hybrid grain parents)
(1999 date, 14 locations, 2 reps/location)

| | Days to flowering | | | Relative maturity for self-pollinated hybrid (days) |
|---|---|---|---|---|
| | 10% | 50% | 90% | |
| LH195SDms × LH185 | 64.8 | 66.4 | 67.8 | 116 |
| LH245SDms × LH283 | 64.8 | 66.4 | 67.9 | 117 |

As shown in Tables 3 and 5, when used as a pollinator in the TOPCROSS® grain production system, P741 produces grain kernels with comparable oil content to those produced using LP57.1 as the pollinator. However, the grain produced using P741 as the pollinator has substantially increased test weight compared to grain produced using LP57.1 as the pollinator.

EXAMPLES OF USING P741 AS A POLLINATOR

Strip test trials were conducted by Holden's Foundation Seeds, L.L.C. in the summer of 1999 to compare the characteristics of grain produced from various hybrids rendered male sterile and pollinated by P741 with the characteristics of grain produced from grow outs of the same hybrids in their fertile state. As Table 3 shows, when P741 was used to pollinate the male sterile grain parent the average oil content of the grain was 2.9 percentage points higher on a dry basis than when the corresponding fertile hybrids were self pollinated. When LP57.1 was used to pollinate the male sterile grain parent the average oil content of the grain was 2.8 percentage points higher on a dry basis than when the corresponding fertile hybrids were self-pollinated. Test weight was 1.5 lb/bu lower in the high oil grain arising on plants pollinated by P741 compared to the grain from the corresponding fertile hybrids. Test weight was 2.4 lb/bu lower in the high oil grain arising on plants pollinated by LP57.1 compared to the grain from the corresponding fertile hybrids. Thus P741 contributed similar oil as LP57.1, but had almost a 1 lb/bu improvement in test weight compared to LP57.1.

TABLE 3

1998 TOPCROSS® Grain Production System Strip Test Results
Using P741 and P57 as Pollinator
Across a Range of Hybrid Grain Parents
Absolute Increase or Decrease Over the Mean Value for Grain
Produced from the Self- and Sib-pollinated Grain Parents

| | Test Weight (lb/bu) | Oil Content (% at 0% moisture) |
|---|---|---|
| P741 blends | −1.5 | +2.9 |
| LP57.1 blends | −2.4 | +2.8 |

Table 4 presents 1999 TOPCROSS® grain production system strip test data for two grain parent hybrids pollinated by P741 at a number of locations. As Table 4 shows, the average level of oil in grain arising from LH200SDms× LH185 pollinated by P741 was 7.25%, with test weight of 55.9 lb/bu, and for LH198SDms×QH102 pollinated with P741 was 9.04% with test weight of 57.3 lb/bu.

TABLE 4

1999 TOPCROSS® Grain Production System Strip Test Data Using
P741 as the pollinator

| Grain Parent | Grain Yield bu/acre | Grain Moisture at Harvest % | Test Weight lb/bu | Oil | Protein | Starch |
|---|---|---|---|---|---|---|
| | | | | \% at 0% moisture | | |
| LH200SDms × LH185 | 152 | 18.1 | 55.9 | 7.25 | 8.76 | 67.67 |
| Number of locations | 34 | 34 | 29 | 26 | 26 | 26 |
| LH198SDms × QH102 | 141 | 19.4 | 57.3 | 9.04 | 9.16 | 65.22 |
| Number of locations | 34 | 34 | 28 | 28 | 28 | 28 |

Table 5 presents data comparing the performance of P741 and LP57.1 when used in TC BLEND® seed blends comprising the same grain parents as in Table 4, LH200SDms× LH185 and LH198SDms×QH102. The data shows that, compared to LP57.1 seed blends, the P741 seed blends are slightly higher yielding at about the same grain moisture and produce grain having only slightly less oil content (average 0.28 percentage points lower across both grain parents) but substantially increased test weight (almost 2 lb/bu more on average).

TABLE 5

Comparison of Performance of P741 and LP57.1 in
TC BLEND® Seed Blends Using the Same Grain Parents

| TC BLEND® Seed Blend | Yield (bu/A) | Moisture % | Test Wt. (lbs/bu) | Oil Content (%, dry basis) | Protein (%, dry basis) |
|---|---|---|---|---|---|
| LH200SDms × LH185 + P741 | 154 | 17.5 | 55.6 | 7.10 | 8.98 |
| LH200SDms × LH185 + P57 | 145 | 17.4 | 54.0 | 7.29 | 9.18 |
| Difference | 9 | 0.1 | 1.6 | −0.19 | −0.20 |
| Locations | 14 | 14 | 10 | 11 | 11 |
| LH19BSDmS × QH102 + P741 | 143 | 18.3 | 57.5 | 8.77 | 9.33 |
| LH198SDms × Q102 + P57 | 140 | 18.5 | 55.4 | 9.14 | 9.81 |
| Difference | 3 | −0.2 | 2.1 | −0.37 | −0.48 |
| Locations | 15 | 15 | 10 | 12 | 12 |

DEPOSIT INFORMATION

Applicant has made available to the public without restriction a deposit under the Budapest Treaty of at least 2500 seeds of maize hybrid P741 with the American Type Culture Collection (ATCC), Manassas, Va. 20110, ATCC Deposit Designation PTA-2978. Parental seed stocks of Qx47 and P732 have also been made available to the public without restriction from a deposit under the Budapest Treaty of at least 2500 seeds of each synthetic population with the American Type Culture Collection (ATCC) under Deposit Designation PTA-2973 for Qx47 and PTA-2974 for P732.

The seeds deposited with the ATCC were taken from the same deposit maintained by Holden's Foundation Seeds, Inc., 503 S. Maplewood Ave., P.O. Box 839, Williamsburg, Iowa 52361 since prior to the filing date of this application. The deposits will be maintained in the ATCC depository, which is a public depository, for a period of 30 years, or 5 years after the most recent request, or for the effective life of the patent, whichever is longer, and will be replaced if they become nonviable during that period.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

What is claimed is:

1. The corn hybrid P741, a representative sample of seeds of which have been deposited with the ATCC under Patent Deposit Designation PTA-2978.

2. A hybrid corn seed designated P741, a representative sample of which has been deposited with the ATCC under Patent Deposit Designation PTA-2978.

3. A hybrid corn plant produced by the seed of claim 2.

4. Pollen of the hybrid corn plant of claim 3.

5. A tissue culture comprising regenerable cells of the hybrid corn plant of claim 3.

6. A corn plant regenerated from regenerable cells of the tissue culture of claim 5 and having all the phenotypic, genotypic and physiological characteristics of the hybrid corn plant designated P741, a representative sample of which has been deposited with the ATCC under Patent Deposit Designation PTA-2978.

7. A corn plant having all the phenotypic, genotypic and physiological characteristics of the hybrid corn plant of claim 3.

8. A method for producing a hybrid corn seed comprising the steps of:
   a) planting in pollinating proximity seeds of corn lines Qx47 (Patent Deposit Designation PTA-2973) and P732 (Patent Deposit Designation PTA-2974);
   b) cultivating corn plants resulting from the planting until the time of flowering;
   c) emasculating the flowers of the plants of either corn line Qx47 or P732;
   d) allowing cross pollination to occur between the lines; and
   e) harvesting seeds produced on the emasculated plants.

9. A seed corn blend comprising a mixture of male sterile hybrid corn seed and the hybrid corn seed of claim 2.

* * * * *